(12) United States Patent
Ray et al.

(10) Patent No.: US 8,026,356 B2
(45) Date of Patent: Sep. 27, 2011

(54) PROCESS FOR THE LARGE SCALE PRODUCTION OF STAVUDINE

(75) Inventors: Purna Chandra Ray, Secunderabad (IN); Jagan Mohana Chary Tummanapalli, Secunderabad (IN); Seeta Ramanjaneyulu Gorantla, Secunderabad (IN)

(73) Assignee: Matrix Laboratories, Ltd., Secunderabad (IN)

( * ) Notice: Subject to any disclaimer, the term of this patent is extended or adjusted under 35 U.S.C. 154(b) by 556 days.

(21) Appl. No.: 12/094,586

(22) PCT Filed: Nov. 17, 2006

(86) PCT No.: PCT/IN2006/000455
§ 371 (c)(1),
(2), (4) Date: May 21, 2008

(87) PCT Pub. No.: WO2007/060689
PCT Pub. Date: May 31, 2007

(65) Prior Publication Data
US 2008/0312428 A1    Dec. 18, 2008

(30) Foreign Application Priority Data
Nov. 28, 2005    (IN) .......................... 1735/CHE/2005

(51) Int. Cl.
*C07H 19/00* (2006.01)
*C07H 19/048* (2006.01)
*C07H 5/04* (2006.01)
*C07H 5/06* (2006.01)
*C08B 37/00* (2006.01)

(52) U.S. Cl. ...................... 536/28.2; 536/55.3

(58) Field of Classification Search ...................... None
See application file for complete search history.

(56) References Cited

U.S. PATENT DOCUMENTS 5,539,099 A    7/1996  Skonezny et al.
6,635,753 B1   10/2003 Radatus et al.

FOREIGN PATENT DOCUMENTS
EP              653435              5/1995

OTHER PUBLICATIONS

Adachi, et al., Charbohydrate Research, (1979), 113.
J.P Horwitz, et al., J. Org. Chem., (1996), 31, 205.
Mansuri, et al., J. Med. Chem., (1989), 32, 461.
International Search Report from PCT/IN20061000455 mailed May 21, 2007.

*Primary Examiner* — Layla Bland
(74) *Attorney, Agent, or Firm* — Knobbe, Martens, Olson & Bear, LLP

(57) ABSTRACT

The present invention provides a method for preparing pure Stavudine having purity more than 99.5% comprises: i) Converting 3',5'-anhydrothymidine to crude Stavudine, ii) Converting crude Stavudine to stable solvates of Stavudine, iii) Desolvation of the solvates to give pure Stavudine. The present invention also disclosed novel solvates of Stavudine and conversion of novel Stavudine solvates to Stavudine.

14 Claims, 2 Drawing Sheets

PROCESS FOR THE LARGE SCALE PRODUCTION OF STAVUDINE

The present invention relates to an improved process for large-scale production of Stavudine through novel solvates of Stavudine

BACKGROUND OF THE INVENTION

2',3'-didehydro-3'-deoxythymidine (Stavudine) has the formula given below.

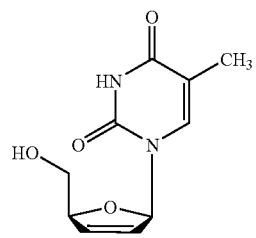

Stavudine is also known as $d_4T$ which is approved by U.S. FDA for the therapeutic treatment of patients infected with retroviruses.

Synthesis of Stavudine is first reported by J. P. Horwitz et al (J. Org. Chem. (1996) 31, 205) starting from 3'4'-dimesylthymidine as shown in Scheme-1.

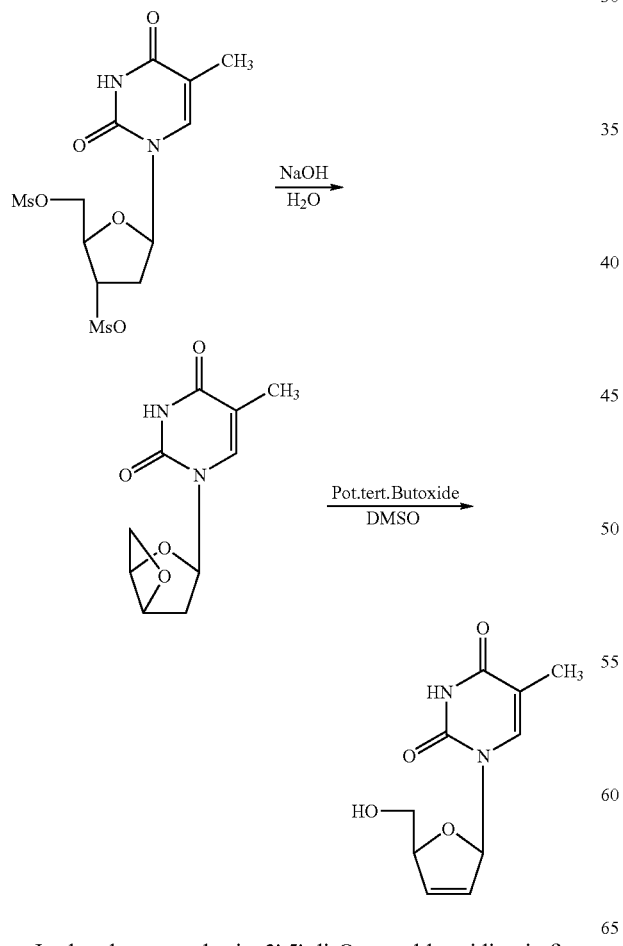

In the above synthesis, 3',5'-di-O-mesylthymidine is first treated with sodium hydroxide in refluxing water for 2 hours and the resultant 3,4-anhydrothymidine is treated with potassium t-butoxide in dimethyl sulfoxide (DMSO) at room temperature for 2 hrs. The reaction mixture is neutralized, evaporated to dryness and after a series of manipulations which included extraction, declourization, precipitation and recrystallization, gave Stavudine in 79% yield and an overall yield of 56%.

The above procedure is modified by Mansuri et al (J. Med. Chem. (1989) 32, 461) where the potassium t-butoxide/DMSO mixture is poured in to 30 volumes of toluene whereby the Stavudine precipitates as the potassium salt along with excess potassium tert-butoxide. This modification avoided the distillation of DMSO which caused decomposition of Stavudine. The obtained salt is neutralized in water and the precipitated product is extracted with acetone and then evaporated to dryness to give an off-white solid in 57% yield.

Adachi et al. [Carbohydrate Research (1979) 113] overcame some of the decomposition problems by employing sodium hydroxide in hexamethyl phosphorictriamide (HMPA). HMPA is removed by forming a chloroform complex in an aqueous mixture and Stavudine is isolated from the aqueous phase.

U.S. Pat. No. 5,539,099 discloses a modified route for producing Stavudine as shown in Scheme-2.

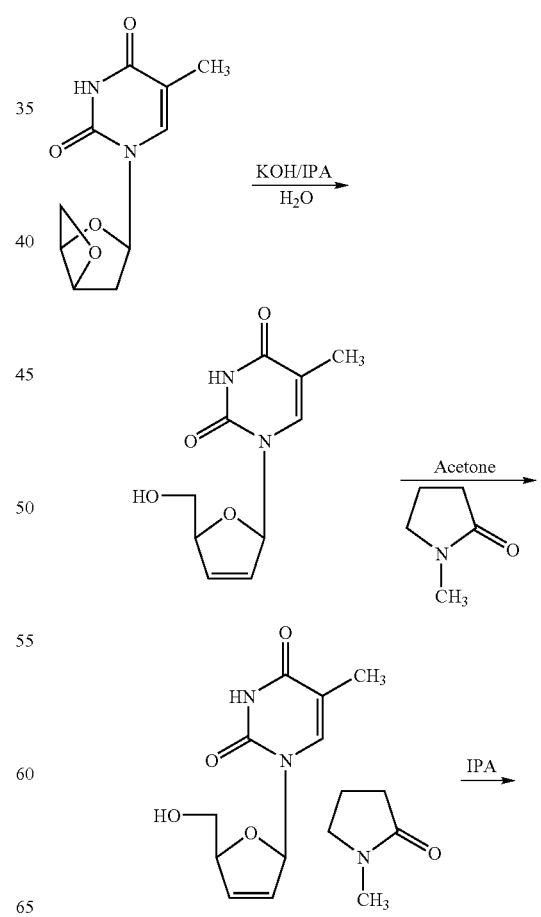

-continued

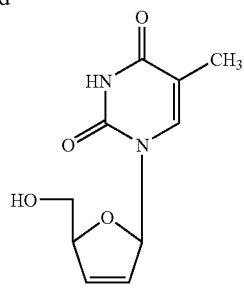
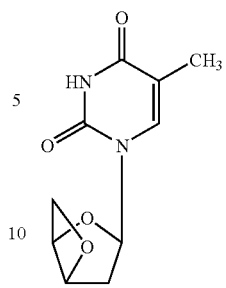
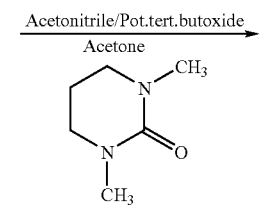
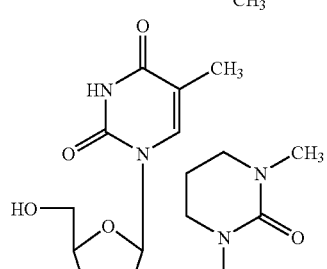

DMPU solvate

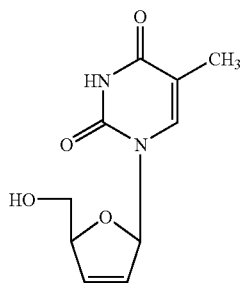

Stavudine

However, all the above discussed processes have one major draw back in common in that the final purity of Stavudine is less than the desired 99.5%. Known impurities which are difficult by using conventional techniques are still present, some of which were thymine, thymidine, threo-thymidine, 3,5-anhydrothymidine and 5'-O-[stavudin-5"-yl]-thero-thymidine being particularly difficult to remove.

Further U.S. Pat. No. 5,539,099 teaches the use of only N-methyl-2-pyrrolidinone as suitable to form a solvate of Stavudine whose recovery requires the use of an aprotic ester, amide or ketone solvent. No consideration is given for their use to form a solvate.

U.S. Pat. No. 6,635,753 discloses the novel Stavudine solvates of N,N-dimethyl acetamide, N,N-dimethylacrylamide, N,N-dimethylpropionamide etc. and recovering substantially pure Stavudine by breaking the solvate produced.

It is therefore an object of this invention to provide an improved process which is more efficient, using less toxic materials (for example, using solvents which are less toxic than N-Methyl-2-pyrrolidinone, DMA, DMAC and DMP) and providing pure product before recrystallization steps are carried out.

SUMMARY OF THE INVENTION

The main object of the present invention is to provide an improved process for producing substantially pure Stavudine on commercial scale.

Another object of the invention is to provide a process for preparing novel solvates of Stavudine by reacting Stavudine with the selected solvent.

Yet another object of the invention is to provide a process or producing substantially pure Stavudine by desolvation of novel solvate of Stavudine.

DETAILED DESCRIPTION OF THE INVENTION

Figure 1:
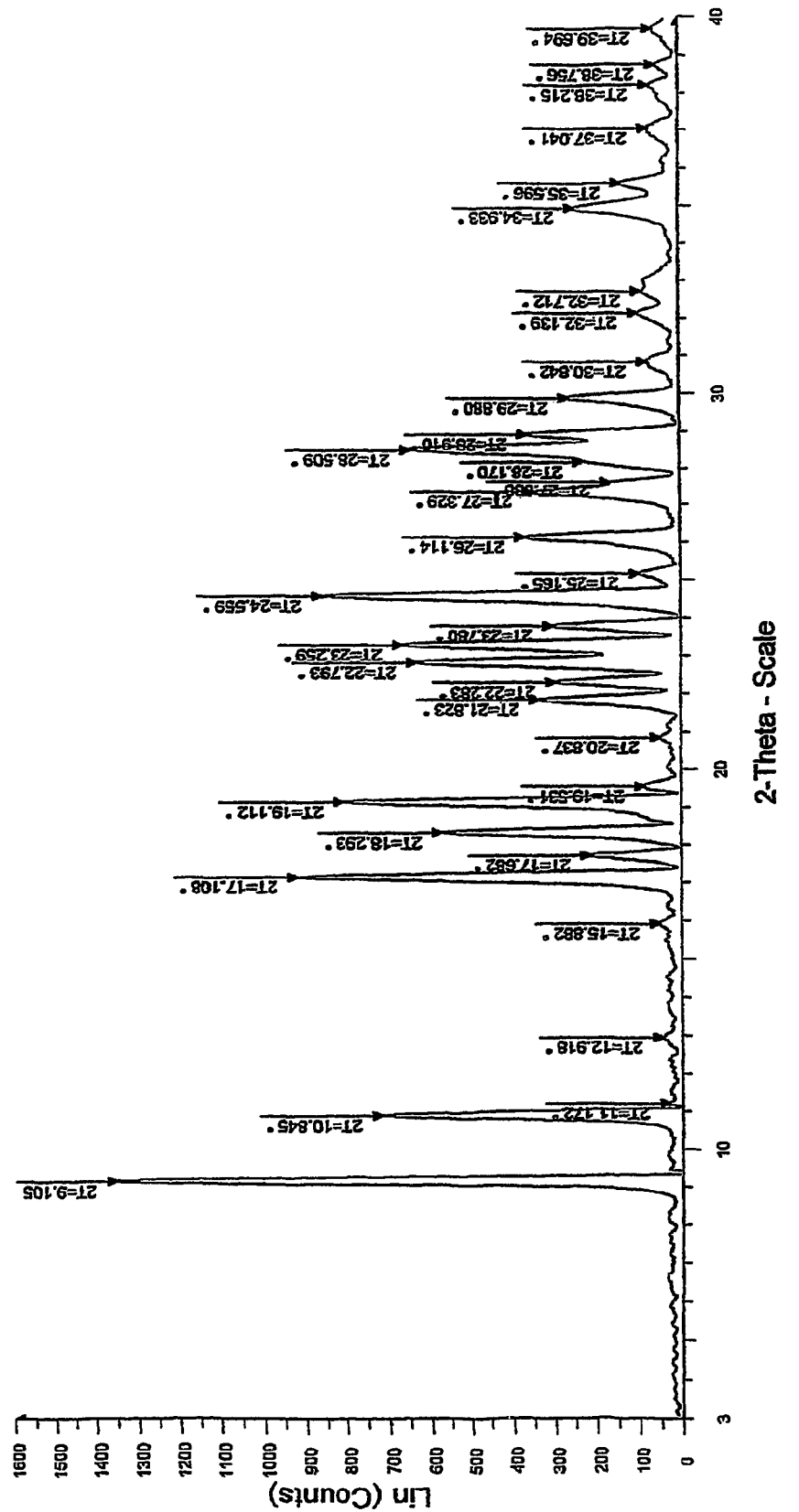
FIG. 1 shows the X-ray diffraction pattern of Stavudine obtained as per example-2
Figure 2:
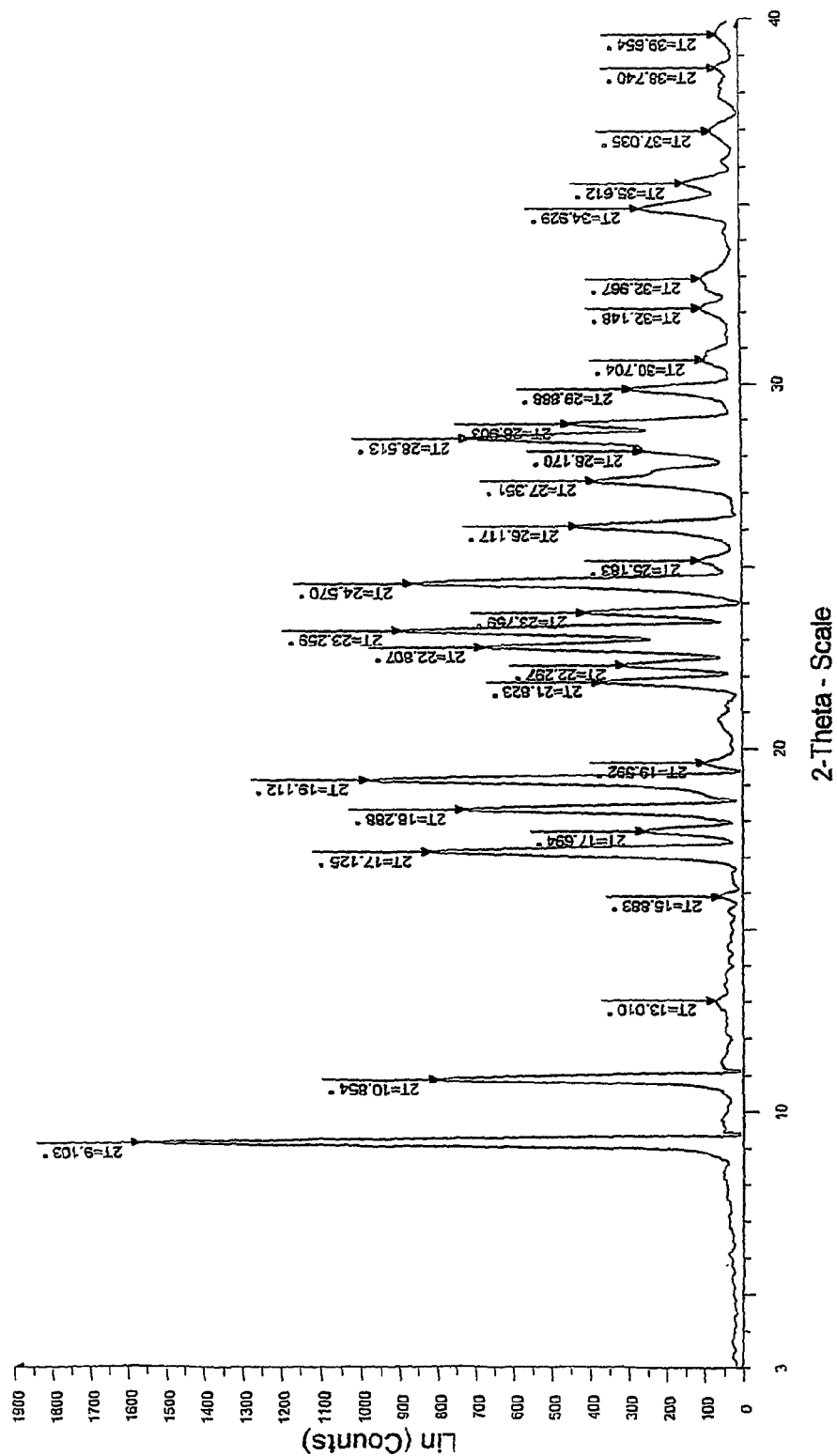
FIG. 2 shows the X-ray diffraction pattern of crystalline Stavudine form-I

Thus in accordance with the present invention process for preparation of substantially pure Stavudine comprising steps of:
Converting 3',5'-anhydrothymidine to crude Stavudine
Converting crude Stavudine to stable solvates of Stavudine
Desolvation of the solvates to give pure Stavudine
The reaction scheme can be expressed as follows.

In a specific embodiment, the present invention provides a process for the preparation of Stavudine, which involves
a) Heating a mixture of 3',5'-anhydrothymidine and potassium tert-butoxide, in acetonitrile to 40°-80° C. preferably 60°-70° C.;
b) Maintaining the reaction mass for about 1 to about 4 hours preferably 2-3 hours
c) Cooling the reaction mass to about 5°-10° C.
d) Dissolving the reaction mass in methanol
e) Neutralizing the reaction mass with an organic acid preferably acetic acid or an inorganic acid preferably Hydrochloric acid,
f) Filtering the reaction mass to remove the salts
g) Evaporating the filtered solution to get crude Stavudine
Further crude Stavudine is converted to its solvates by
a) Charging the crude Stavudine in an organic solvent which is selected from an alcohol wherein the alcohol is selected from the group consisting of methanol, ethanol, n-propanol, 2-propanol, 1-butanol and iso butanol, ketone wherein the ketone is selected from the group consisting of acetone, methyl ethyl ketone and methyl isobutyl ketone and heating to reflux
b) Filtering the solution while hot condition through hyflow
c) Treating the filtered solution with a compound selected from N,N-Dimethylpropyleneurea, N,N-Dimethylethylenurea and their mixtures thereof in an organic solvent d) Precipitating the solvated form of Stavudine and a solvent selected from N,N-Dimethypropyleneurea, N,N-Dimethylethyleneurea and their mixtures thereof e) Filtering the product of step d) to obtain the solvated form of Stavudine and a solvent selected from N,N-Dimethypropyleneurea, N,N-Dimethyl ethyleneurea and their mixtures thereof The prepared Stavudine DMPU solvate and Stavudine DMEU solvate are novel. They are identified and characterized by chemical analysis, NMR & Mass spectral data. Stavudine solvates are further converted to Stavudine by a) Suspending Stavudine solvate in a solvent which is selected from water, alcohol wherein the alcohol is selected from the group consisting of methanol, ethanol, 1-propanol, 2-propanol, 1-butanol and iso butanol, ketone wherein the ketone is selected from the group consisting of acetone, methyl ethyl ketone and methyl isobutyl ketone and an amide other than those which form solvates b) Heating the suspension to 40° C. to reflux temperature preferably to 50°-60° C. for dissolution c) Treating with activated carbon d) Filtering the mass while hot condition preferably through hyflow e) Cooling the clear filtrate to 0° C. to room temperature preferably 0° C. to 5° C.

f) Isolating the precipitated product g) Drying the product to give pure Stavudine having purity more than 99.5%

The obtained Stavudine is crystalline in nature and the XRD resembles polymorphic form I both in wet and dry product. The XRD of the obtained product is mentioned in FIG. 1

The % purity of the product obtained by this process generally exceeds 99.5% and in some instances exceeds 99.80%.

Several advantages in carrying out embodiments of the invention include but are not limited to the following:

When the crystallization solvent is essentially DMPU, the impurity levels are very low which is especially important for thymine and stavudinyl-threo-thymidine impurities since they are particularly difficult to remove using conventional techniques.

N,N-Dimethylpropyleneurea is a more common, more readily available, less hazardous, and less toxic solvent than N-Methyl-2-pyrrolidinone (NMPO), N,N-Dimethylacetamide and other solvents disclosed in the prior art.

In sum the new improved process for producing Stavudine and related analogs is amenable to large-scale use by virtue of its selection of regents, reaction conditions, and separation/purification features that result in an efficient process minimizing troublesome impurities and product degradation as well as providing a high yield and purity of product without generation of its that are either toxic or produced in large scale.

Example-1

Preparation of 2',3'-Didehydro-3'-deoxythymidine-N, N-dimethyl propylene urea Solvate (Stavudine DMPU Solvate)

3',4'-anhydrothymidine (25 g, 0.116 mole) is suspended in acetonitrile (300 ml). The slurry is stirred and potassium tert-butoxide (25 g, 0.2232 mole) is added. The resulting solution is heated to 60-65° C. for 2 hrs. The solution is cooled to 5-10° C., separated salt is filtered under nitrogen atmosphere and immediately dissolved in methanol (200 ml). pH of the solution is adjusted to 6.5 with conc. HCl and cooled to 20° C. The precipitated KCl is filtered and washed with methanol (25 ml). The combined filtrate and wash are concentrated under vacuum. To the residue acetone (250 ml), is added and heated to reflux for 0.5 hrs. Reaction mass is filtered while hot and washed with hot acetone (25 ml). Combined filtrate and wash are mixed with N,N-dimethylpropyleneurea (27 ml) and concentrated until about 100 ml of acetone remained. The solution is allowed to cool to 0-5° C., filtered, washed with acetone (25 ml) to give a total of 27.6 g (70.2%) of the title compound.

Example-2

Preparation of 2',3'-didehydro-3'-deoxythymidine (Stavudine)

Stavudine DMPU solvate (25 g, 0.060 mole) is dissolved in isopropanol (250 ml), and treated with activated carbon antieno crowns (2.5 g) at reflux temperature. Reaction mass is filtered while hot and washed with hot isopropanol (25 ml). The combined filtrate and wash are concentrated to 100 ml and allowed the mass to cool to room temperature slowly. Cooled the mass to 0-5° C. and the precipitated product is filtered. washed the product with chilled isopropanol (10 ml) and air dried to give 13.2 g (83%) of the title compound which purity greater than 99%. XRD data resembles crystalline form-I General Procedure Stavudine-N,N-Dimethyl propylene urea (DMPU) Solvate from Crude Stavudine Method A:

Crude Stavudine (25 g, 95.79% pure, 0.116 mole) is dissolved in N,N-Dimethyl propylene urea (30.0 g, 1.2 parts) at 85-90° C. The solution is allowed to cool to room temperature. The mixture is further cooled to 6-8° C. and maintained for 2 hrs. The crystals are filtered, washed with acetone (2×12 ml) and dried to give white Stavudine.DMPU solvate (33.5 g, 84.9%) with a chromatographic purity of 99.87%.

MP: 120° and SOR $[\alpha]^{25}=-27.5$ (c=1; water)

The Bruker Avance 300 MHz 1H NMR spectrum in DMSO d6 showed δ 1.72 (s, 3H, Stavudine, CH3), 1.86 (m, 2H); 2.75 (s, 2×3H, N(CH3)2); 3.2 (m, 4H, 2×CH2); 3.60 (m, 2H, 2×H-5'); 4.77 (s, 1H, H-4); 5.02 (t, —OH); 5.91 (dd, 1H, H-2'); 6.39 (dl, 1H, H-3'); 6.82 (d, 1H, H-1'); 7.64 (s, 1H, H-6); 11.30 (s, 1H, NH). The Stavudine position of the above spectrum agrees with the literature values (J. Med. Chem. 32 461 (1989).

Method B:

Crude Stavudine (25 g, 96.7% pure, 0.1116 mole), N,N-dimethyl propylene urea (37.5 g, 1.5 parts) are added to isopropanol (50 ml, 2 volumes) and heated to 70-75° C. for dissolution. The obtained solution is stirred for 15 min. at 75° C. and cooled to 6-8° C. The precipitated product is filtered, washed with IPA and dried to give 34.1 g of Stavudine DMPU solvate (86.7%) with a chromatographic purity of 99.91%

Method C:

Crude Stavudine (25 g, 97.7% pure, 0.1116 mole), DMPU (37.5 g, 1.5 parts) are added to acetone (50 ml) and heated to 56° C. for dissolution. The obtained solution is stirred for 15 min. at 56° C. and cooled to 6-8° C. The precipitated product is filtered, washed with acetone and dried to give 34.4 g of Stavudine DMPU solvate (87.5%) with a chromatographic purity 99.93%.

The following Table 1 summarizes the improvements in chromatographic purity for the above examples.

TABLE 1

| Method | Starting | Chromatographic purities % | | | | |
|---|---|---|---|---|---|---|
| | | Stavudine | Thymidine | Threothymidine | Oxetane | Stavudinyl-threothymidine |
| A | Stavudine | 95.79 | 0.68 | 0.45 | 0.08 | 0.62 |
| A | Stavudine DMPU | 99.87 | 0.08 | — | — | — |
| B | Stavudine | 96.77 | 0.42 | 0.27 | 0.09 | 0.54 |
| B | Stavudine DMPU | 99.91 | 0.09 | — | — | — |
| C | Stavudine | 97.77 | .28 | 0.21 | 0.07 | 0.43 |
| C | Stavudine | 99.93 | 0.07 | — | — | — |

The above three methods were presented to illustrate different ways of obtaining the Stavudine DMPU solvate. Method A showed Stavudine and the solvent being combined, heated to dissolve, cooled to crystallize and then isolated. Methods B and C illustrated the use of protic and aprotic solvents such as isopropanol and acetone to aid in the filtration (prevents premature crystallization during filtration) of the solution to remove inorganic salts.

Isolation of Pure Stavudine from Stavudine DMPU Solvate:

Method D:

Stavudine DMPU solvate (20 g, 0.057 mole) is dissolved in water (20 ml) at 55° C. and the solution is allowed cooling on its own for an hour to crystallize. The mixture is further cooled on 0-5° C. for 2 hrs. The precipitated product is filtered, washed with acetone and dried to give 8.5 g (66.82%) of pure white crystalline Stavudine. HPLC results are given in Table-2

Method E:

Stavudine DMPU solvate (20 g, 0.057 moles), water (3.6 ml) and acetone (289 ml) and heated to 55° C. and the hot solution is filtered. The clear filtrate is distilled until about 70 ml of acetone remained. The solution is allowed to cool on its own and at about 40° C. it is seeded with pure Stavudine. Cooled the mass to 0-5° C. and stirred for 1 hr. The precipitated product is filtered, washed with chilled acetone (2×12 ml) and dried to give 10.68 g (84%) pure product. The HPLC results are given in Table-2.

Method F:

Stavudine-DMPU solvate (25 g, 0.07 moles), water (5 g) and isopropanol (250 ml) are heated to about 82° C. to get clear colorless solution. Heating is continued so as to distill the solution at atmospheric pressure until about 80 ml of isopropanol remained in side. The solution is allowed to cool on its own. The mixture is further cooled to 0-5° C. for 1.5 hrs. The precipitated product is filtered, washed with isopropanol (2×10 ml) and air dried to give 13.9 g (87.2%) of pure white crystalline Stavudine. The HPLC results are given in Table 2.

The above three examples illustrate the use of three different solvent systems for breaking the solvate and isolating pure Stavudine.

The DMEU solvate can be prepared and desolvated similarly as DMPU solvate to get pure Stavudine.

As many changes can be made to the embodiments without departing from the scope of the invention, it is intended that all material contained herein be illustrative of the invention and not be interpreted in a limiting sense

We claim:

1. A solvated form of Stavudine, wherein the solvent is selected from N,N-Dimethylpropyleneurea (DMPU) or N,N-Dimethylethyleneurea (DMEU).

2. The solvated form of Stavudine of claim 1, wherein the solvated form of Stavudine is Stavudine N,N-Dimethylpropyleneurea solvate.

3. The solvated form of Stavudine of claim 1, wherein the solvated form of Stavudine is Stavudine N,N-Dimethylethyleneurea solvate.

4. A process for making the solvated form of Stavudine of claim 1 comprising the steps of;
   a) reacting Stavudine with a solvent selected from N,N-Dimethylpropyleneurea or N,N-Dimethylethyleneurea;
   b) precipitating the solvated form of Stavudine and a solvent selected from N,N-Dimethylpropyleneurea or N,N-Dimethylethyleneurea; and
   c) filtering the product of step b) to obtain the solvated form of Stavudine and a solvent selected from N,N-Dimethylpropyleneurea or N,N-Dimethylethyleneurea.

5. The process as claimed in claim 4, wherein in the step a) the reaction is performed in an organic solvent selected from alcohol or ketone.

6. The process as claimed in claim 5, wherein the alcohol is selected from the group consisting of methanol, ethanol, 1-propanol, 2-propanol, 1-butanol and isobutanol.

7. The process as claimed in claim 5, wherein the ketone is selected from the group consisting of acetone, methyl ethyl ketone and methyl isobutyl ketone.

8. An improved process for the preparation of Stavudine comprising the steps of:

TABLE 2

| Method | Stavudine DMPU (g) | Stavudine (g) | % Yield | Purity (%) | | | | |
|---|---|---|---|---|---|---|---|---|
| | | | | Stavudine | Thymine | Threo-thymidine | Oxetane | Stavudinyl threothymidine |
| D | 20 | 8.5 | 66.82 | 99.68 | 0.14 | — | — | — |
| E | 20 | 10.68 | 84.00 | 99.82 | 0.07 | — | 0.06 | 0.05 |
| F | 24 | 12.6 | 82.54 | 99.80 | 0.09 | — | 0.06 | 0.05 | a) heating 3',5'-anhydrothymidine in acetonitrile in potassium t-butoxide;
b) adding methanol to the reaction mass;
c) neutralizing with an acid and filtering the reaction mass to remove the insoluble salts;
d) evaporating the solvent from the filtered mass;
e) dissolving the crude Stavudine in an organic solvent which is selected from alcohol or ketone, wherein the alcohol is selected from the group consisting of methanol, ethanol, n-propanol, 2-propanol, 1-butanol and isobutanol, and the ketone is selected from the group consisting of acetone, methyl ethyl ketone and methyl isobutyl ketone;
f) treating with a solvent selected from the group consisting of N,N-Dimethylpropyleneurea, N,N-Dimethylethyleneurea and their mixtures thereof in an organic solvent to precipitate corresponding Stavudine solvate which is isolated from the reaction mixture; and
g) desolvating the Stavudine solvate in a solvent is selected from water, alcohol, or ketone, wherein the alcohol is selected from the group consisting of methanol, ethanol, 1-propanol, 2-propanol, 1-butanol and isobutanol, and the ketone is selected from the group consisting of acetone, methyl ethyl ketone and methyl isobutyl ketone.

9. The process as claimed in claim 8, wherein the step a) is carried out at reflux temperature.

10. The process as claimed in claim 8, wherein in the step g) said desolvating is carried out at room temperature to reflux temperature.

11. The process as claimed in claim 8, wherein the solvent in step e) is an alcohol selected from the group consisting of methanol, ethanol, 1-propanol, 2-propanol, 1-butanol and isobutanol.

12. The process as claimed in claim 8, wherein the solvent in step e) is a ketone selected from the group consisting of acetone, methyl ethyl ketone and methyl isobutyl ketone.

13. The improved process as claimed in claim 8, wherein the obtained Stavudine from the process is in crystalline form-I of which powder X-Ray Diffraction (XRD) Pattern is shown in FIG. 1.

14. The process as claimed in claim 10, wherein said reflux temperature is at 50-60° C.

* * * * *

UNITED STATES PATENT AND TRADEMARK OFFICE
CERTIFICATE OF CORRECTION

| | | |
|---|---|---|
| PATENT NO. | : 8,026,356 B2 | Page 1 of 1 |
| APPLICATION NO. | : 12/094586 | |
| DATED | : September 27, 2011 | |
| INVENTOR(S) | : Purna Chandra Ray et al. | |

It is certified that error appears in the above-identified patent and that said Letters Patent is hereby corrected as shown below:

On Page 1 (Item 56) column 2 at line 8, under Other Publications, change "Charbohydrate" to --Carbohydrate--

On Page 1 (Item 56) column 2 at line 11, under U.S. Patent Documents, change "PCT/IN20061000455" to --PCT/IN2006/000455--

Col. 1 at line 6, change "Stavudine" to --Stavudine.--

Col. 2 at line 5, change "declourization," to --decolourization,--

Col. 4 at lines 66-67, change "N,N-Dimethylethylenurea" to --N,N-Dimethylethyleneurea--

Col. 5 at line 2, change "N,N-Dimethypropyleneurea," to --N,N-Dimethylpropyleneurea,--

Col. 5 at lines 5-6, change "N,N-Dimethypropyleneurea," to --N,N-Dimethylpropyleneurea,--

Col. 5 at line 33, change "1" to --1.--

Col. 6 at line 26, change "filtered." to --filtered,--

Col. 6 at line 29, change "form-I" to --form-I.--

Col. 6 at line 39, change "Stavudine. DMPU" to --Stavudine DMPU--

Col. 6 at line 57, change "99.91%" to --99.91%.--

Col. 7 at line 33, change "Table-2" to --Table-2.--

Col. 8 at approximately line 24, change "sense" to --sense.--

Signed and Sealed this
Twenty-fourth Day of April, 2012

David J. Kappos
*Director of the United States Patent and Trademark Office*